United States Patent [19]

Miller et al.

[11] Patent Number: 4,892,108
[45] Date of Patent: Jan. 9, 1990

[54] MULTI-CHANNEL EXTRACOCHLEAR IMPLANT

[75] Inventors: Josef M. Miller; Bryan E. Pfingst, both of Ann Arbor, Mich.; Anders Tjellstrom, Gothenburg; Tomas Albrektsson, Molndal, both of Sweden

[73] Assignee: The Regents of the University of Michigan, Ann Arbor, Mich.

[21] Appl. No.: 76,882

[22] Filed: Jul. 23, 1987

[51] Int. Cl.$^4$ ............................................. A61N 1/00
[52] U.S. Cl. .................................... 128/784; 128/420.6
[58] Field of Search .................. 128/420.5, 784, 420.6, 128/640, 642, 789, 419 P

[56] References Cited

U.S. PATENT DOCUMENTS

| H356 | 11/1987 | Stokes et al. | 128/419 P |
|---|---|---|---|
| 4,066,085 | 1/1978 | Hess | 128/419 P |
| 4,177,818 | 12/1979 | De Pedro | 128/419 P |
| 4,261,372 | 4/1981 | Hansen et al. | 128/784 |
| 4,390,756 | 6/1983 | Hoffmann et al. | 128/419 R |
| 4,400,590 | 8/1983 | Michelson | 179/107 FD |
| 4,462,401 | 7/1984 | Burgio | 128/789 |
| 4,462,402 | 7/1984 | Burgio et al. | 128/419 R |
| 4,485,268 | 11/1984 | Kaplan | 174/84 C |
| 4,487,210 | 12/1984 | Knudsen et al. | 128/785 |
| 4,495,953 | 1/1985 | Bennewitz | 128/789 |
| 4,510,936 | 4/1985 | Fourcin et al. | 128/419 R |
| 4,532,930 | 8/1985 | Crosby et al. | 128/419 R |
| 4,536,844 | 8/1985 | Lyon | 179/107 FD |
| 4,592,359 | 6/1986 | Galbraith | 128/419 R |
| 4,606,329 | 8/1986 | Hough | 128/1 R |
| 4,611,596 | 9/1986 | Wasserman | 128/419 R |
| 4,611,598 | 9/1986 | Hortmann et al. | 128/419 R |
| 4,612,915 | 9/1986 | Hough et al. | 128/1 R |
| 4,617,913 | 10/1986 | Eddington | 128/1 R |
| 4,622,975 | 11/1986 | Danby et al. | 128/642 |
| 4,641,664 | 2/1987 | Botvidsson | 128/419 P |
| 4,648,403 | 3/1987 | Van Compernolle | 128/419 R |

Primary Examiner—Francis Jaworski
Assistant Examiner—George Manuel
Attorney, Agent, or Firm—Harness, Dickey & Pierce

[57] ABSTRACT

A titanium anchoring device for anchoring at least one electrode in or adjacent to a human cochlea so that the electrode can afford electrical stimulation of nerve fibers to produce the sensation of sound includes a titanium shaft disposed in an aperture in the lateral wall of the inner ear. At least one titanium barb is formed about the shaft for preventing removal of the shaft from the aperture. At least one aperture is formed to communicate axially through the shaft to allow the electrode to be disposed within the shaft.

21 Claims, 2 Drawing Sheets

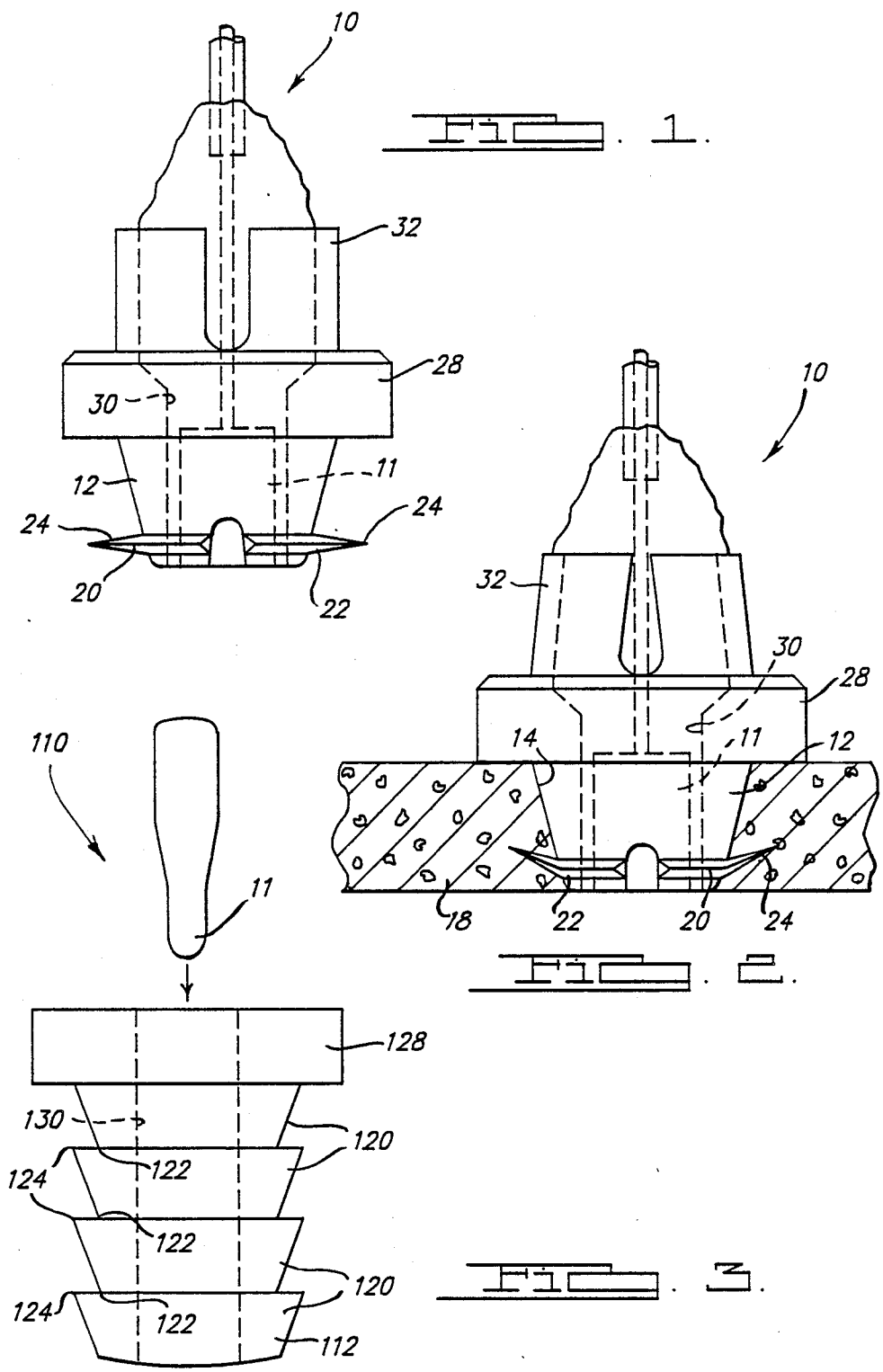

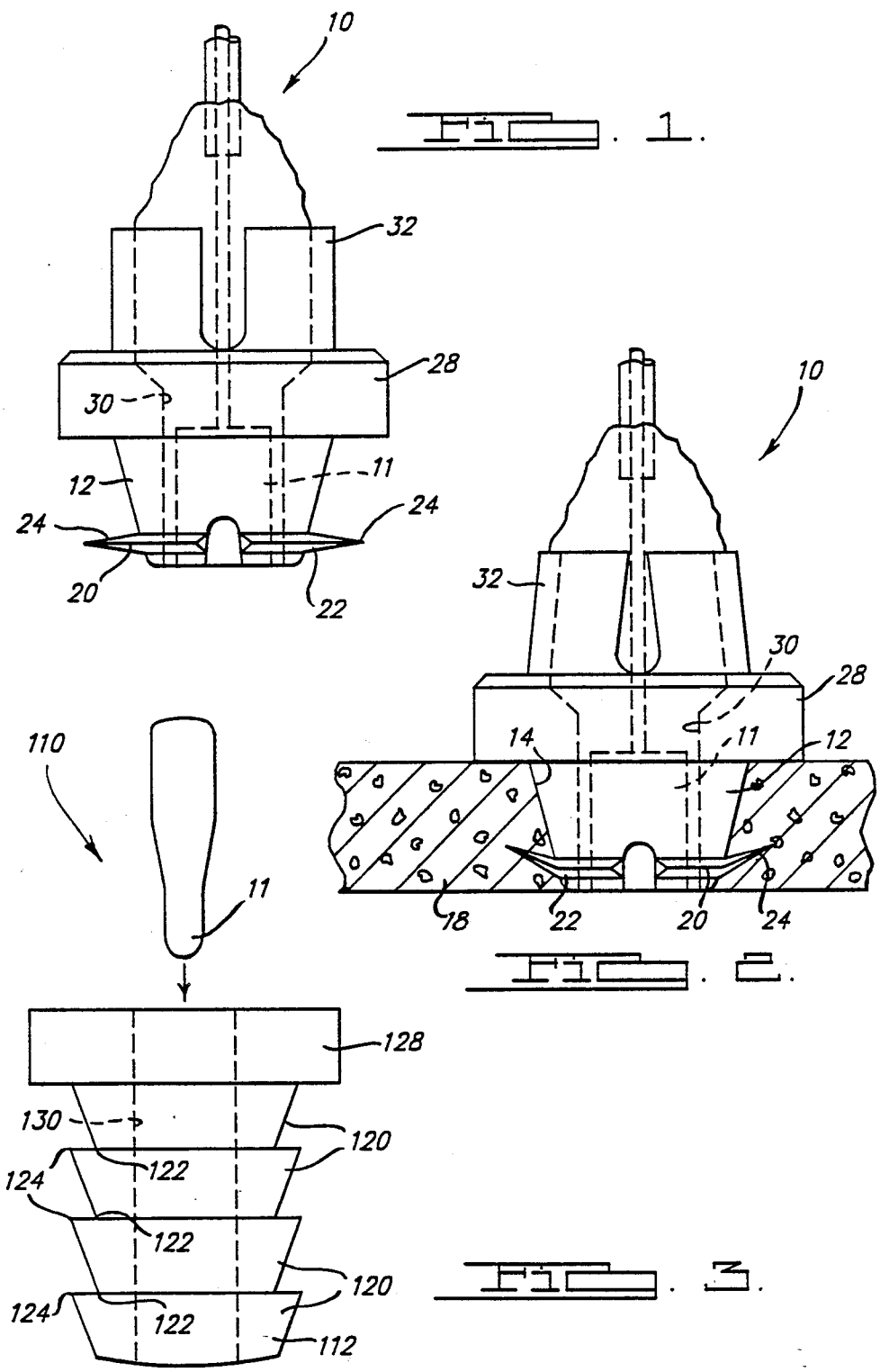

MULTI-CHANNEL EXTRACOCHLEAR IMPLANT

TECHNICAL FIELD

The subject invention relates to a device used in implanting electrodes near or adjacent the human cochlea.

BACKGROUND OF THE INVENTION

In the development of a multi-channel prosthesis, data from the study of radially versus longitudinally arranged pairs of electrodes relative to the spiral lamina, the effects of distance between electrode pairs, and the electroanatomy of the cochlear tissues and fluids, suggest that electrode pairs should be close together and in close proximity to neural elements of the spiral lamina to maximize channel independence in multi-electrode devices. Data concerning insertion trauma and safe limit of stimulation, suggests that the implant size should be small and that electrode surface areas should be large and sufficiently removed from excitable elements to minimize the effects of very high local current densities at their surfaces on these tissues. In addition, existing evidence supports the view that we may lose little in perceptual benefits and gain significantly in safety characteristics by placing electrodes outside the otic capsule.

The technical difficulties with the development of such a multi-channel middle ear system include the creation of precise holes through the bony lateral wall with minimum damage to the underlying cochlear tissues at predetermined sites, and the anchoring of stimulating electrodes in the fenstrae.

In the past, several types of devices have been used to anchor electrodes. Examples of such anchoring devices are disclosed in U.S. Pat. No. 4,462,402, issued Jul. 31, 1984, to Burgio et al.; U.S. Pat. No. 4,487,210, issued Dec. 11, 1984, to Knudsen et al.; U.S. Pat. No. 4,612,915, issued Sept. 23, 1986, to Hough et al.; and U.S. Pat. No. 4,606,329, issued Aug. 19, 1986, to Hough. The problem is that these anchoring devices have been used at bony sites of the body, including recently, the temporal bone, but not the otic capsule.

SUMMARY OF THE INVENTION AND ADVANTAGES

An anchoring device for anchoring at least one electrode in or adjacent to a human cochlea so that the electrode can afford electrical stimulation of nerve fibers to produce the sensation of sound includes a shaft means forming a cylindrical shaft and being disposed in an aperture in the lateral wall of the inner ear. A barb means forms at least one barb about the shaft means for preventing removal of the shaft means from the aperture. An aperture means forms at least one aperture communicating axially through the shaft means to allow the electrode to be disposed within the shaft means.

Accordingly, the subject invention stays in place once implanted. Microscopic assessment indicates bony contact with the implant surface. The extent of bony contact varied from 30%–50% with the implant surface. Detailed analysis revealed only patches of bone tissue in direct contact with the implant. The bone was of a primitive rather than a Haversian structure, but sufficient to hold the implant in place.

FIGURES IN THE DRAWINGS

Other advantages of the present invention will be readily appreciated as the same becomes better understood by reference to the followed detailed description when considered in connection with the accompanying drawings wherein:

FIG. 1 is an elevational view of a preferred embodiment of the subject invention;

FIG. 1 is an elevational view of the preferred embodiment of FIG. 1 implanted; and FIG. 3 is an elevation view of an alternate embodiment of the subject invention.

DESCRIPTION OF THE PREFERRED EMBODIMENT

An anchor device for anchoring at least one electrode in or adjacent to a human cochlea so that the electrode can afford electrical stimulation of nerve fibers to produce the sensation of sound is generally shown at 10 in FIGS. 1 and 2. The anchor device 10 includes shaft means forming a shaft 12 having a frustoconical shape and being disposed in an aperture 14 in the lateral wall 18 of the inner ear. The anchor device 10 acts as an anchor point for stimulating electrode. Such a stimulating electrode may be made of platinum or eridium. The anchor device 10 allows contact of the stimulating electrode with the lateral surface of the membranous labyrinth.

The anchoring device 10 also includes barb means forming at least one barb 20 about the shaft 12 for preventing removal of the shaft 12 from the aperture 14. The barb 20 is annular in configuration and disposed about or near one end of the shaft 12. The shaft 12 and barb 20 are integral and made of titanium, such as commercially pure (99.7%), non-alloyed titanium. The barb has a first end 22 connected to the shaft 12 and a second end 24 extending radially outwardly from the shaft 12. The first end 22 is axially thicker than the second end 24. The barb 20 is yieldable from a first to a second position to allow insertion of the shaft 12 in the aperture 14 and to prevent removal of the shaft 12 from the aperture 14.

The anchoring device 10 also includes stop means attached to the shaft 12 for allowing the shaft 12 to be inserted in the aperture 14 a predetermined distance. The stop means comprises a flange 28 extending radially outwardly from the shaft 12 at the end opposite the barb 20. The flange 28 is also made of titanium and may be integral with the shaft 12 and barb 20.

The anchoring device 10 further includes aperture means 20 forming at least one aperture 30 communicating axially through the shaft 12 to allow the electrode to be disposed within the shaft 12. An adhesive material secures the electrode 11 in engagement with the wall of the aperture 30.

The anchoring device includes crimp means connected to the shaft 12 about the aperture 30 and adapted to be crimped for preventing the electrode 11 from exiting the aperture 30. The crimp means comprises a second flange 32 extending axially outwardly from one end of the shaft 12. The second flange 32 may also be made of titanium and be integral with the shaft 12.

An alternate embodiment of the subject invention, wherein like parts have like numerals increased by one hundred (100), is generally shown at 110 in FIG. 3. The anchor device 110 has a series of axially spaced barbs 120. This allows the anchor device 110 to act as a "screw" when inserted into the aperture 14.

The invention has been described in an illustrative manner, and it is to be understood that the terminology which has been used is intended to be in the nature of words of description, rather than of limitation.

Obviously, many modifications and variations of the present invention are possible in light of the above teachings. It is, therefore, to be understood that that within the scope of the appended claims, the invention may be practiced otherwise than as specifically described.

What is claimed is:

1. An anchor device for anchoring at least one electrode in or adjacent to a human cochlea so that the at least one electrode can afford electrical stimulation of nerve fibers to produce the sensation of sound, said device comprising:
    shaft means forming a shaft and adapted to be disposed in an aperture in the lateral wall of the inner ear;
    barb means forming at least one barb about said shaft means for preventing removal of said shaft means from the aperture; and
    aperture means forming at least one aperture communicating axially through said shaft means to allow the at least one electrode to be disposed within said shaft means;
    wherein said barb means comprises an annular barb disposed about said shaft means near one end thereof.

2. A device as set forth in claim 1 including stop means attached to said shaft means for allowing said shaft means to be inserted in the aperture a predetermined distance.

3. A device as set forth in claim 2 wherein said stop means comprises a flange extending radially outwardly from said shaft means.

4. A device as set forth in claim 3 wherein said flange is made of titanium.

5. A device as set forth in claim 2 wherein said barb means comprises a plurality of axially spaced barbs.

6. A device as set forth in claim 5 wherein said shaft means is made of titanium.

7. A device as set forth in claim 6 wherein said barbs are made of titanium.

8. A device as set forth in claim 1 wherein said shaft means comprises a shaft made of titanium.

9. A device as set forth in claim 1 wherein said barb is made of titanium.

10. A device as set forth in claim 1 wherein said barb has a first end connected to said shaft and a second end extending radially outwardly from said shaft.

11. A device as set forth in claim 10 wherein said first end of said barb is axially thicker than said second end.

12. A device as set forth in claim 11 wherein said barb is yieldable from a first to a second position to allow insertion of said shaft in the aperture and to prevent removal of said shaft from the aperture.

13. A device as set forth in claim 12 wherein said second end of said barb includes an arcuate portion.

14. A device as set forth in claim 1 including crimp means connected to said shaft means about said aperture means and adapted to be crimped for preventing the at least one electrode from exiting said aperture means.

15. A device as set forth in claim 14 wherein said crimp means comprises a second flange extending axially outwardly from one end of said shaft means.

16. A device as set forth in claim 15 wherein said flange is made of titanium.

17. An anchor device for anchoring at least one electrode in or adjacent to a human cochlea so that the at least one electrode can afford electrical stimulation of nerve fibers to produce the sensation of sound, said device comprising:
    shaft means forming a shaft and adapted to be disposed in an aperture in the lateral wall of the inner ear;
    barb means forming at least one barb about said shaft means for preventing removal of said shaft means from the aperture;
    aperture means forming at least one aperture communicating axially through said shaft means to allow the at least one electrode to be disposed within said shaft means;
    stop means attached to said shaft means for allowing said shaft means to be inserted in the aperture a predetermined distance;
    said shaft means comprising a shaft being made of titanium; and
    said barb means comprising a continuous annular barb disposed about said shaft near one end thereof and being made of titanium.

18. A device as set forth in claim 17 wherein said barb has a first end connected to said shaft and a second end extending radially outwardly from said shaft, said first end being axially thicker than the second end.

19. A device as set forth in claim 18 wherein said stop means comprises an annular flange extending radially outwardly from said shaft at the end opposite said barb and being made of titanium.

20. A device as set forth in claim 19 wherein said barb is yieldable from a first to a second position to allow insertion of said shaft in the aperture and to prevent removal of said shaft from the aperture.

21. An anchor device for anchoring at least one electrode in or adjacent to a human cochlea so that the at least one electrode can afford electrical stimulation of nerve fibers to produce the sensation of sound, said device comprising:
    shaft means forming a shaft and adapted to be disposed in an aperture in the lateral wall of the inner ear;
    barb means forming at least one barb about said shaft means for preventing removal of said shaft means from the aperture;
    aperture means forming at least one aperture communicating axially through said shaft means to allow the at least one electrode to be disposed within said shaft means;
    stop means attached to said shaft means for allowing said shaft means to be inserted in the aperture a predetermined distance;
    crimp means connected to said shaft means about said aperture and adapted to be crimped for preventing the at least one electrode from exiting said aperture;
    said shaft means comprising a shaft made of titanium;
    said barb means comprising a barb disposed about said shaft near one end thereof and is made of titanium;
    said barb is yieldable from a first to a second position to allow insertion of said shaft in the aperture and to prevent removal of said shaft from the aperture;
    said barb having a first end connected to said shaft and extending radially outwardly from said shaft, said first end is axially thicker than said second end;
    said stop means comprising an annular flange extending radially outwardly from said shaft at the end opposite said barb and is made of titanium; and
    said crimp means comprising an annular second flange extending axially outwardly from one end of said shaft and is made of titanium.

* * * * *